(12) United States Patent
Gilbert et al.

(10) Patent No.: US 8,012,338 B2
(45) Date of Patent: Sep. 6, 2011

(54) METHOD FOR PREPARING BIOMEDICAL SURFACES

(75) Inventors: Jeremy Gilbert, Fayetteville, NY (US); Zhijun Bai, Halifax (CA); Nithya Chandrasekaran, Dorchester, MA (US)

(73) Assignee: Syracuse University, Syracuse, NY (US)

( * ) Notice: Subject to any disclaimer, the term of this patent is extended or adjusted under 35 U.S.C. 154(b) by 1142 days.

(21) Appl. No.: 11/673,674

(22) Filed: Feb. 12, 2007

(65) Prior Publication Data

US 2007/0187253 A1 Aug. 16, 2007

Related U.S. Application Data

(60) Provisional application No. 60/766,781, filed on Feb. 10, 2006.

(51) Int. Cl.
*C25F 3/08* (2006.01)
(52) U.S. Cl. ......... 205/674; 205/200; 205/212; 205/640
(58) Field of Classification Search .................. 205/200, 205/212, 640, 674
See application file for complete search history.

(56) References Cited

U.S. PATENT DOCUMENTS

| | | | | |
|---|---|---|---|---|
| 4,923,513 | A * | 5/1990 | Ducheyne et al. | 75/245 |
| 6,565,735 | B1 * | 5/2003 | Fortunati et al. | 205/704 |
| 6,920,677 | B2 * | 7/2005 | Dolan et al. | 29/557 |
| 7,229,545 | B2 * | 6/2007 | Sewing et al. | 205/170 |
| 7,780,838 | B2 * | 8/2010 | Ostrovsky | 205/200 |
| 2002/0143398 | A1 * | 10/2002 | Osaka et al. | 623/11.11 |
| 2004/0055675 | A1 * | 3/2004 | Kuramoto et al. | 148/669 |
| 2006/0137995 | A1 * | 6/2006 | Ghosh et al. | 205/674 |

* cited by examiner

*Primary Examiner* — Alexa D. Neckel
*Assistant Examiner* — Nicholas A. Smith
(74) *Attorney, Agent, or Firm* — David L. Nocilly; George R. McGuire; Bond Schoeneck & King

(57) ABSTRACT

A method for selectively dissolving the beta (β) phase of a titanium alloy out of the surface of the alloy, thereby leaving behind a nano-scale porous surface having enhanced bonding properties with either a biological tissue, such as bone, or an adhesive material, such as a polymer or ceramic by immersing the alloy in an ionic aqueous solution containing high levels of hydrogen peroxide and then exposing the alloy to an electrochemical voltage process resulting in the selective dissolution of the beta phase to form a nano-topographic metallic surface.

13 Claims, 7 Drawing Sheets

METHOD FOR PREPARING BIOMEDICAL SURFACES

CROSS-REFERENCE TO RELATED APPLICATIONS

This application claims priority to U.S. Provisional Patent Application Ser. No. 60/766,781, filed Feb. 10, 2006.

BACKGROUND OF THE INVENTION

1. Field of the Invention

The present invention relates to biomedical surfaces and, more specifically, to a method of preparing biomedical surfaces for enhanced biological interaction and adhesion with adjoining materials or tissue.

2. Description of the Related Art

Porous surfaces have been used for over two decades to provide places for biological fixation between implant and tissue to take place. Typically these porous surfaces are processed by sintering, diffusion bonding, plasma spraying or other mechanism and create rough bead-like or fiber-like surfaces. The spaces between these materials then serve as sites where bone or other tissue can in-grow and attach to the implant. This process is called biological fixation and is used extensively in implants (e.g., dental, hips and knees) to fix the device directly into the bony substrate.

Nano-scale surface topography of implants has gained in interest in recent years as it is becoming known that nano-topography of surfaces can have a significant effect on cell behavior on such nano-topographically modified surfaces. Conventional nano-scale topography formation is directed toward forming nanotubes or nanocolumns using etching/electrochemical processing. Other processes involve making electropolished surfaces. These techniques are frequently very expensive to implement and are of reduced value in surfaces having recessed cavities. As a result, bone attachment is not always successful.

BRIEF SUMMARY OF THE INVENTION

It is a principal object and advantage of the present invention to provide a method for forming biomedical surfaces having nanoscale topography that is electrochemical.

It is an additional object and advantage of the present invention to provide a method for forming biomedical surfaces having nanoscale topography that provides faster, stronger and more robust interfacial adhesion to biological systems.

It is a further object and advantage of the present invention to provide a method for forming biomedical surfaces having nanoscale topography that is less costly.

It is a further object and advantage of the present invention to provide a method for forming biomedical surfaces having nanoscale topography that is applicable for use in connection with recessed cavities.

Other objects and advantages of the present invention will in part be obvious, and in part appear hereinafter.

In accordance with the foregoing objects and advantages, the present invention comprises a process for selectively dissolving one phase of a titanium alloy (the beta ($\beta$) phase of Ti-6Al-4V) out of the surface of the alloy, thereby leaving behind a nano-scale porous surface having enhanced bonding properties with either a biological tissue, such as bone, or an adhesive material, such as a polymer or ceramic. The alloy is immersed into an ionic aqueous solution containing high levels of hydrogen peroxide and then exposed to an electrochemical voltage process resulting in the selective dissolution of the beta phase. With specific voltage conditions and ranges of hydrogen peroxide concentrations surfaces of two phase titanium alloys made from Ti-6Al-4V can be induced to selectively dissolve one phase, thereby forming a nanotopographic metallic surface.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
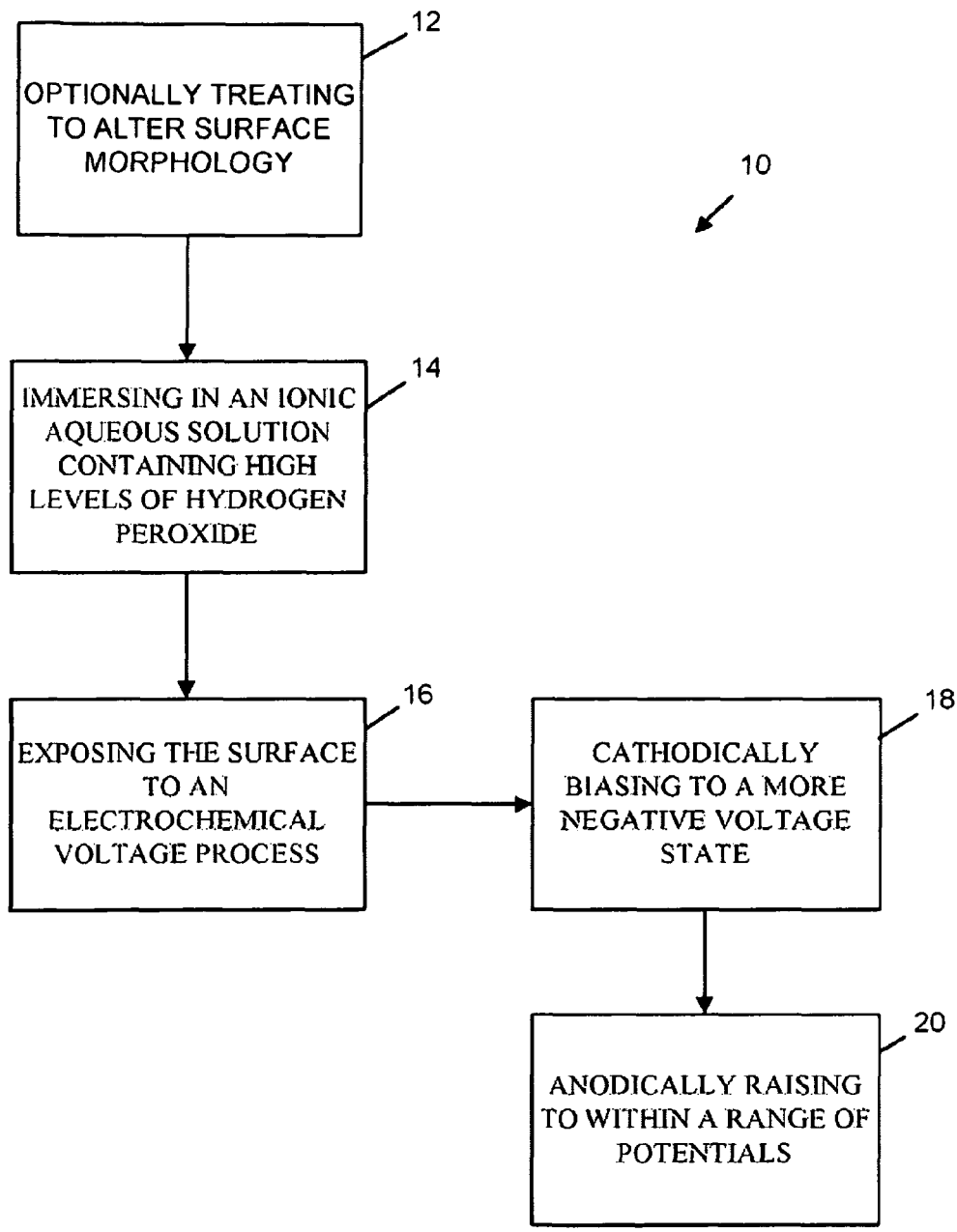
FIG. 1 is a flowchart of a process according to the present invention.

Referring now to the drawings, wherein like reference numerals refer to like parts throughout, the present invention comprises a method of preparing metallic biomedical surfaces for enhanced biological interaction and/or enhanced adhesion with an adjoining material or tissue. The process involves a combination of a chemical and electrochemical interaction between a multiphase titanium alloy, e.g., Ti-6Al-4V, a two phase alloy system used in medical devices (ASTM F-136), and an electrochemical solution, e.g., a 0.154 M solution of phosphate buffered saline modified by the addition of hydrogen peroxide in a molar concentration range of 0.3 to 5.0 M (or broader). The electrochemical solution in conjunction with a specific voltage process causes the surface of the alloy to undergo selective dissolution of one of the two phases of the alloy, thereby leaving a nanotopographic surface roughness and modified oxide film character that provides enhanced ability of the metal surface to interact with adjacent tissues or materials. Single phase titanium alloys (commercially pure titanium, grade 2, ASTM F-67 "Standard Specification for Unalloyed Titanium for Surgical Implant Applications") may also have nanotopographic changes that result from similar processes where the resulting surface appears pitted. The method of the present invention may also create a bioactive gel-likeoxide coating seen in non-electrochemically-driven surface modifications.

Referring to FIG. 1, in a process 10 according to the present invention for preparing nanotopographical surfaces, the alloy selected for preparation may optionally be treated to prepare or alter its surface morphology 12. For example, the alloy may be mechanically polished with emory paper and/or $Al_2O_3$ particles suspended in water to yield a flat polished surface. Alternatively, the alloy may be heated into its beta-phase region (e.g., above about 920° C.) to transforms the microstructure when cooled back to room temperature into a Widmanstatten structure that generally comprises needles/plates of alpha phase encased in beta phase, and thus provides a surface morphology having fingers of alpha with grooves around them.

Process 10 next involves immersing the alloy into an ionic aqueous solution containing high levels of hydrogen peroxide 14, and then exposing the surface to an electrochemical voltage process 16 resulting in the selective dissolution of the beta phase. Surfaces of titanium alloys are covered with nanometer scale metal oxide films (known as passive oxide films or conversion coatings) that result from the reaction of the surface metal with oxygen. These oxide films serve as tenacious barrier coatings that limit subsequent electrochemical (corrosion) reactions and provide the high corrosion resistance of these alloys. The oxide films on titanium alloys result in titanium alloys being known as the most biocompatible metals in use in medical devices today. When these surfaces are exposed to most aqueous electrolyte solutions, they remain in a passive state and will not allow enhanced corrosion reactions to take place. Also, when titanium is exposed to high concentrations of hydrogen peroxide (with no external application of voltage), the effects of selective dissolution do not take place. However, with specific voltage conditions and ranges of hydrogen peroxide concentrations, the surfaces of two phase titanium alloys (made from Ti-6Al-4V) can be induced to selectively dissolve one phase.

To induce the selective dissolution effect, electrochemical voltage process 16 comprises a two-stage process of cathodically biasing 18 the surface of the alloy relative to its open circuit potential to a more negative voltage state (e.g., $-1$V vs Ag/AgCl reference electrode), and then anodically raising the surface 20 of the alloy to within a range of potentials to induce the selective dissolution effect. The Ti-6Al-4V alloy may be cathodically biased to $-1$V Ag/AgCl for a period of several minutes. The surface of the alloy is then brought up to a more anodic potential (e.g., 0V Ag/AgCl) and allowed to sit at this potential for a period of time. If the electrochemical history is not applied and just a positive potential is applied, then selective dissolution effect will not occur. Afterward, the surfaces may be cleaned, dried and imaged in a scanning electron microscope to determine the effect of process 10 on the nanotopography of the alloy.

Hydrogen peroxide in an aqueous phosphate buffered saline solution is preferably used as the ionic aqueous electrolyte solution to selectively dissolve the beta phase of Ti-6Al-4V. There is a range of hydrogen peroxide concentrations that will result in this process and below which it will not occur. A solution of hydrogen peroxide of 0.3 to 1M is needed to induce the selective dissolution effect, but it may also occur (at different rates) with solution ranges outside the 0.3 M to 1M range. Although it is not clear what precise lower limit concentration can induce this effect, the alloy will not selectively dissolve in the absence of hydrogen peroxide.

Figure 2A:
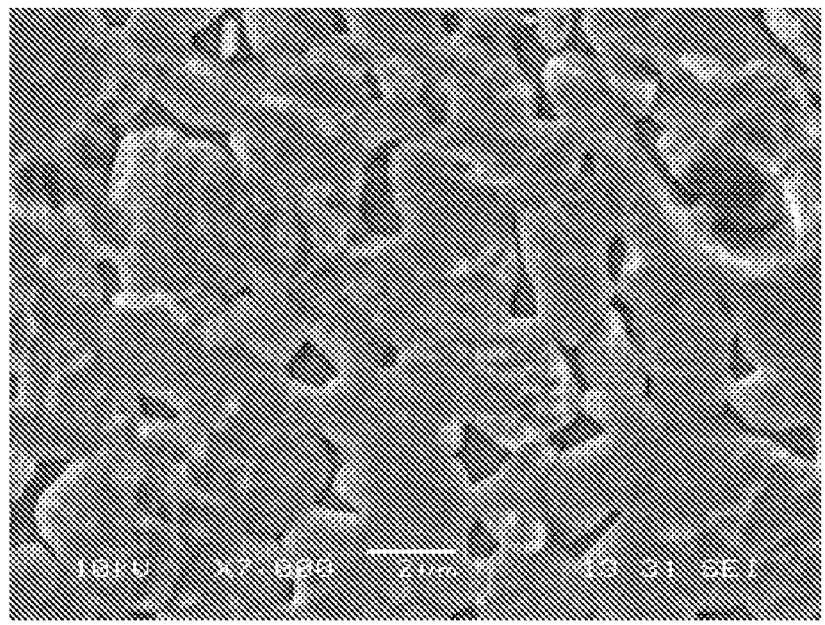
FIGS. 2(a)-(b) are Scanning Electron Micrographs of Ti-6Al-4V: (a) at 7000× after treatment with hydrogen peroxide and electrochemical treatment showing selective dissolution of the beta phase; and (b) at 3500× after standard etching treatments with the beta phase still intact.

FIG. 2a shows an example of an alloy prepared in this manner. The resultant surface shows that the beta grains of the Ti-6Al-4V alloy have been selective dissolved, thereby leaving behind small (micron-size and smaller) surface pits into which biological tissue (e.g., bone cells, etc.) can grow and attach. It is likely that the process dissolves both the alpha and the beta phases, however, it appears that the beta phase is preferentially dissolved at a higher rate.

Figure 2B:
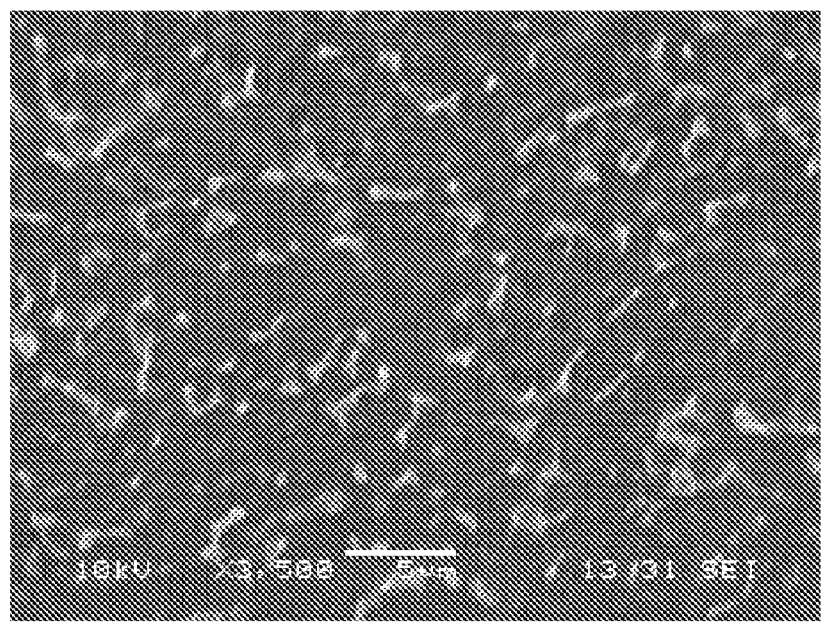

FIG. 2b is of the same alloy after exposure to a standard etching solution (Kroll's Reagent) to reveal the typical microstructure of both alpha and beta phases. One can compare the results from both treatments to see where the selective dissolution has occurred.

Figure 3:
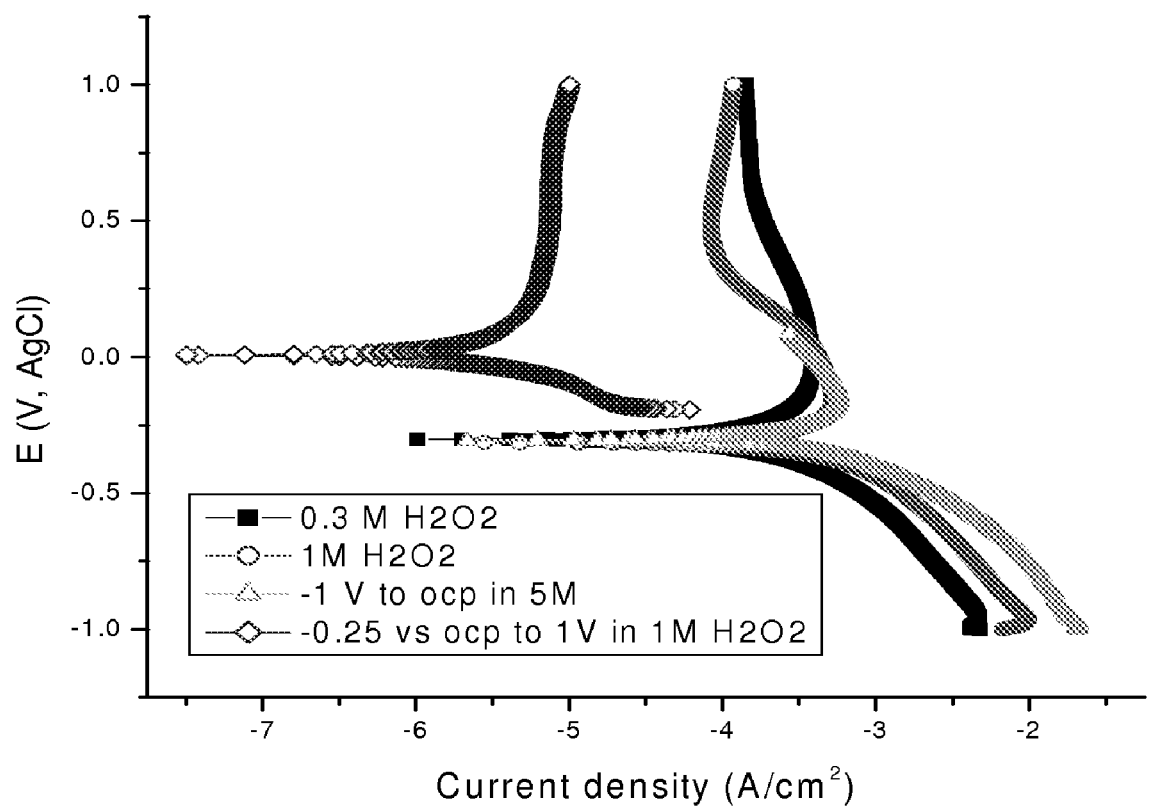
FIG. 3 is a graph of potentiodynamic polarization plots of Ti-6Al-4V in hydrogen peroxide containing solutions.

FIG. 3 shows polarization curves for Ti-6Al-4V in $H_2O_2$ containing solutions where the alloy is first cathodically biased to $-1$V and then poteniodynamically scanned anodically. In performing the cathodic bias, the surface becomes much more active (with higher reduction currents observed compared to non-cathodically biased samples). When these surfaces are brought into the active region for corrosion, then the selective dissolution process can take place. It appears that hydrogen peroxide concentrations that will do this well are in the 1 M range. Note that when the surface is not first cathodically biased (the blue diamonds curve), the current density remains relatively low indicating that the surface oxide is still intact over the entire surface. However, the other surfaces were cathodically biased to $-1$V for a period of time and then scanned anodically. The corrosion currents are one to two orders of magnitude higher and indicate much more active corrosion ongoing. When the alloy is in the active region of the curves (around 0 V), then this is where good quality selective dissolution of the beta phase takes place (after an initial cathodic bias).

Figure 4:
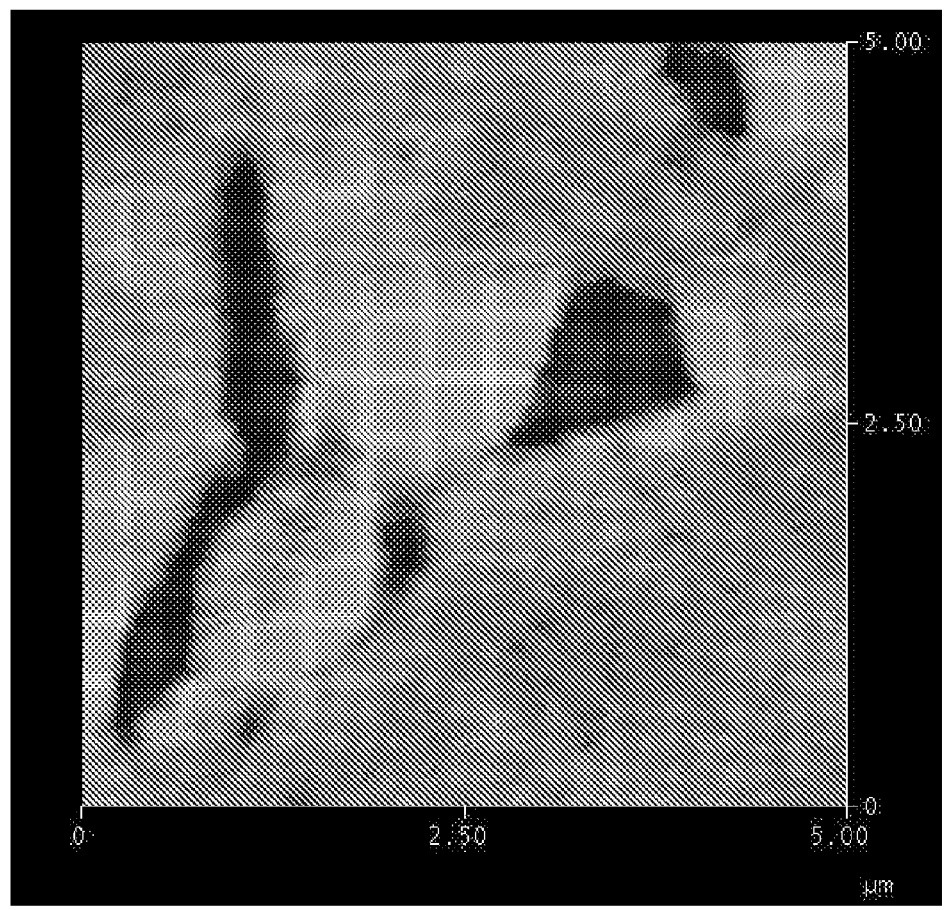
FIG. 4 is a reproduction of an Atomic Force Microscopy image (height) of Ti-6Al-4V after selective dissolution of beta crystals (dark regions of image).

Atomic force microscopy imaging of Ti-6Al-4V, seen in FIG. 4, shows that the alpha phase surface oxide is also modified by the method of the present invention and may influence the interaction between the alloy and the biological system. The retained alpha phase surfaces show a porous hydrated oxide surface having beneficial effects on biological interaction along with the nanotopographic pits in the surface.

Example 1

Figure 5:
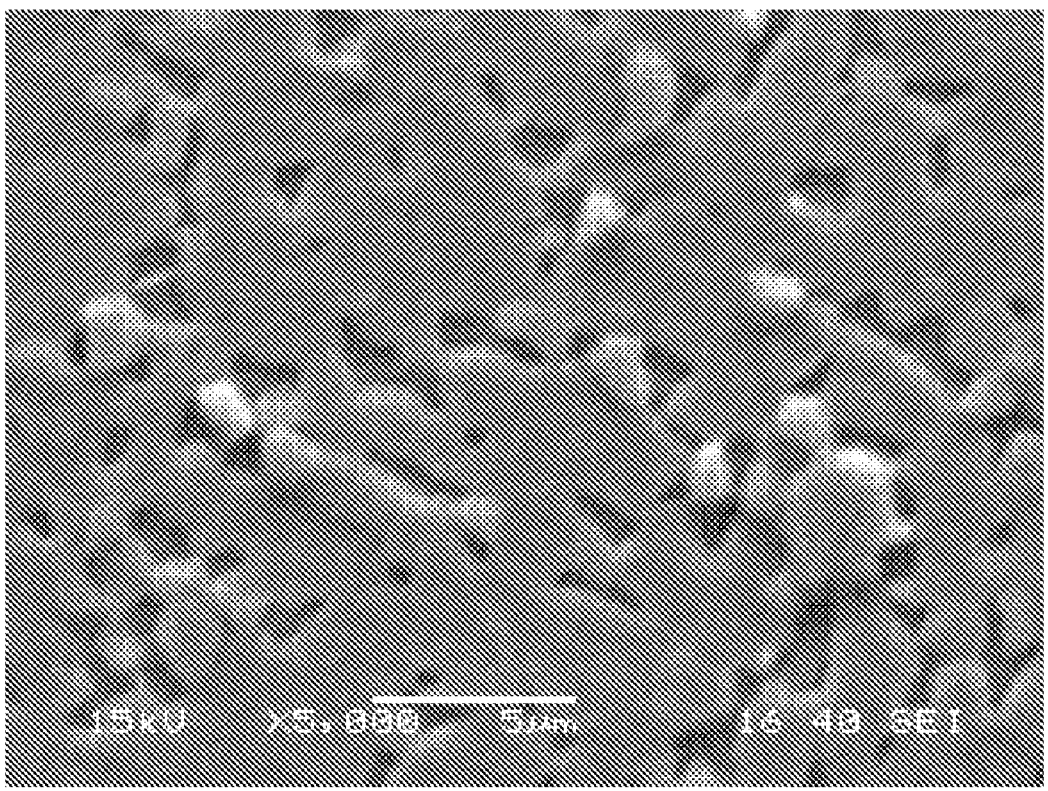
FIG. 5 is a SEM micrograph of Ti-6Al-4V after selective dissolution of beta phase.

Samples of medical grade Ti-6Al-4V-ELI (Extra-low-interstitial, ASTM F136 "Standard Specification for Wrought Titanium 6AL-4V ELI Alloy for Surgical Implant Applications") were mechanically polished with increasing grit emory paper followed by polishing with 1.0, 0.3 and 0.05 µm $Al_2O_3$ particles suspended in water to yield a flat polished surface. These samples were then placed in an electrochemical cell and immersed in a PBS-$H_2O_2$ solution consisting of 0.154 M phosphate buffered saline (Sigma-Aldrich), and modified with 1 M $H_2O_2$. The sample was then electrochemical held at a voltage of $-1$V vs Ag/AgCl for 10 min, afterward the potential of the surface was scanned anodically at 1 mV/s up to 1 V vs Ag/AgCl. At the end of this potential scan, the sample was removed from the solution, rinsed in DI water and allowed to dry. Afterward the sample was placed in the scanning electron microscope and imaged under secondary electrons. The resultant surface is seen in FIG. 5. The beta phase crystals of the microstructure have been selective etched away.

Example 2

Figure 6A:
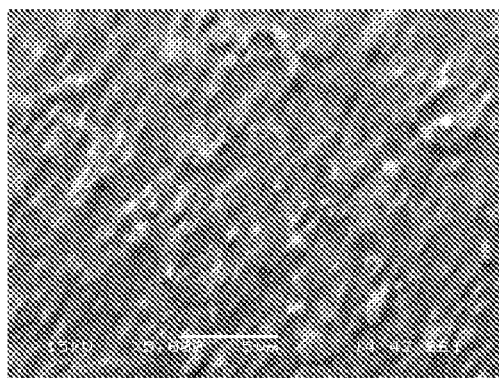
FIGS. 6(a)-(c) are SEM micrographs of Ti-6Al-4V after processing as described in Example 2: (a) holding for 1000 s at −0.5 V; (b) Holding for 1000 s at −0.1 V; and (c) holding for 1000 s at 0.1 V.
Figure 6B:
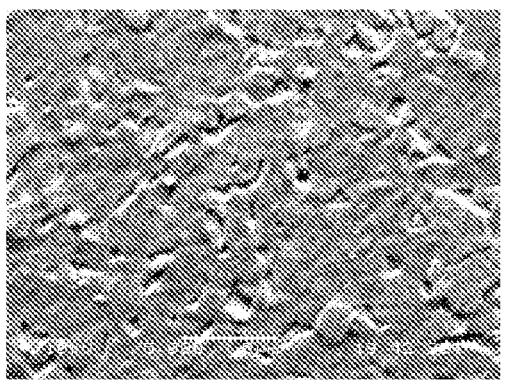
Figure 6C:
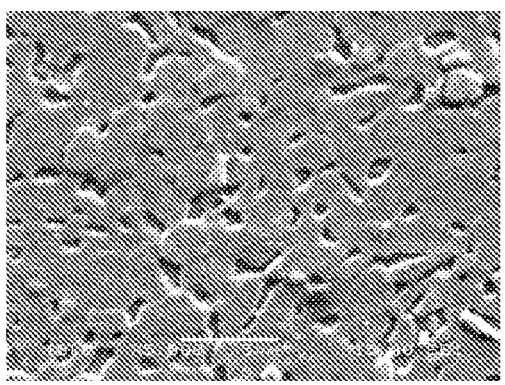

Samples of Ti-6Al-4V were prepared as in example 1 above. In this process, the sample is first held at a cathodic potential ($-1$V vs Ag/AgCl) for a period of 10 minutes and then immediately scanned up to more positive potentials at 1 mV/s and then held fixed for periods of time (typically 1000 s). The potential explored were: $-0.5$V, $-0.1$ V, and 0.1 V. These last two potentials relate to the active region of the polarization plots shown in FIG. 2, while $-0.5$V is still in the somewhat-cathodic potential region. The solution used to perform this was the same as that example 1 (1M $H_2O_2$ in PBS). After the process was complete, the samples were removed from the solution, rinsed in DI water, dried and imaged in the SEM. The results of Example 2 are seen in FIG. 6. The −0.5 V case (a) did not selectively dissolve the beta phase, while the other two (b) and (c) did.

Example 3

Figure 7:
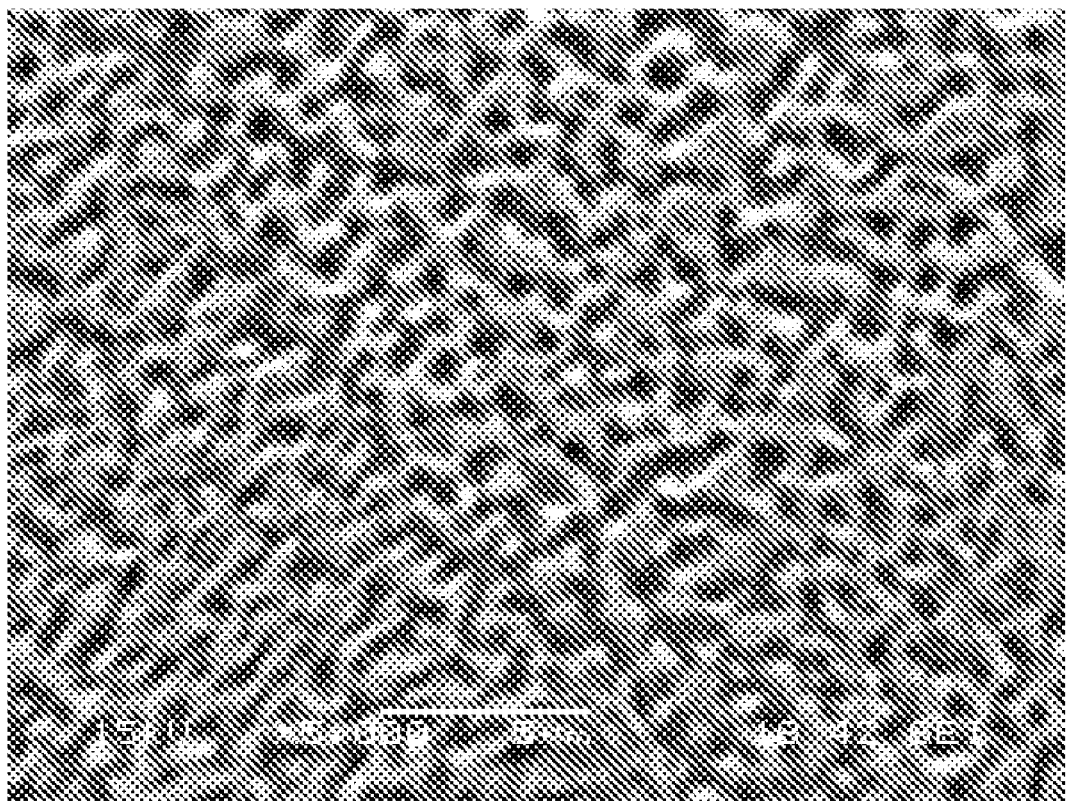
FIG. 7 is a SEM micrograph of Cp-Ti after processing in 1 M $H_2O_2$ PBS solution.

The processed alloy was a commercially pure titanium alloy (ASTM F-36, grade 2). It was prepared and tested as described in example 1, where the potential was first held cathodic at −1.0 V and then scanned anodically to +1.0 V at 1 mV/s. Afterward, it was rinsed dried and imaged as above. The results are seen in FIG. 7, and indicate that the Cp-Ti surface developed micron-scale and nano-scale pits in the surface.

The method of the present invention may thus be used for the preparation of Ti-alloy surfaces for implantation into biological systems to enhance the interaction between the body and the implant. This process could be applied to a wide variety of medical devices where implant-tissue interactions are important. These include bone implant devices, dental implants and potential cardiovascular implants. The resulting effect allows modification of surfaces of titanium alloys to develop micron or smaller (nano-scale) surface topographic features that may enhance these surfaces ability to bond to other materials so it may have applications in metal adhesive technology. There are additional advantages to the method of the present invention in that the beta phase usually contains increased levels of vanadium, which is feared to diminish or reduce the biocompatibility of the surface. Selective removal of this vanadium-rich phase from the surface of these titanium implants may enhance the overall biocompatibility of the device and provide faster, stronger or more robust interfacial adhesion to the biological system. In addition, the gel-like oxide film may have the capability to enhance breakdown of inflammatory mediators and diminish inflammatory response in the short term, and may also enhance the biocompatibility of the surface such as inducing hydroxapatite (HA) coating formation in vivo.

What is claimed is:

1. A method of preparing a metallic biomedical surface, comprising the steps of:
    positioning a three-dimensional, non planar surface comprising a titanium alloy having an alpha and a beta phase in an electrochemical cell;
    immersing said alloy in a non-acidic, ionic aqueous electrolyte solution containing hydrogen peroxide;
    cathodically biasing said alloy to a negative voltage state for a first predetermined time period; and
    raising the anodic potential of the alloy for a second predetermined period of time to selectively dissolve the beta phase of the alloy.

2. The method of claim 1, wherein said alloy comprises Ti-6Al-4V.

3. The method of claim 1, wherein said first predetermined period of time is about ten minutes.

4. The method of claim 1, wherein the step of cathodically biasing said alloy to a negative voltage state for a first predetermined time period comprises electrochemically holding said alloy at a voltage of −1V.

5. The method of claim 1, wherein said ionic aqueous electrolyte solution comprises a phosphate buffered saline solution modified with hydrogen peroxide.

6. The method of claim 5, wherein said solution comprises hydrogen peroxide in a molar concentration range of 0.3 to 5.0 M.

7. The method of claim 6, wherein said solution comprises 0.154 M phosphate buffered saline modified with 1 M hydrogen peroxide.

8. A method of preparing a metallic biomedical surface, comprising the steps of:
    positioning a titanium alloy in an electrochemical cell;
    immersing said alloy in an ionic aqueous electrolyte solution containing hydrogen peroxide;
    cathodically biasing said alloy to a negative voltage state for a first predetermined time period by electrochemically holding said alloy at a voltage of −1 V; and
    raising the anodic potential of the alloy for a second predetermined period of time by anodically scanning said alloy at 1 mV per second to a voltage of 1 V.

9. A method of preparing a metallic biomedical surface, comprising the steps of:
    positioning a three-dimensional, non planar surface comprising a titanium alloy having an alpha and a beta phase in an electrochemical cell;
    immersing said alloy in a non-acidic, phosphate buffered solution of saline and hydrogen peroxide;
    cathodically biasing said alloy to voltage state of about −1V for a predetermined time period; and
    raising the anodic potential of the alloy to a voltage of about to selectively dissolve the beta phase of the alloy.

10. The method of claim 9, further comprising the step of preparing the surface of said titanium alloy before positioning said titanium alloy in said electrochemical cell.

11. The method of claim 10 wherein the step of preparing the surface of said titanium alloy comprises mechanically polishing said titanium alloy.

12. The method of claim 11, wherein mechanically polishing said titanium alloy comprises polishing with aluminum oxide particles suspended in water.

13. The method of claim 12, wherein the step of preparing the surface of said titanium alloy comprises the steps of heating said titanium alloy into the beta-phase region of said titanium alloy and cooling said titanium alloy, thereby forming a Widmanstatten structure.

* * * * *